(12) United States Patent
Lombardo et al.

(10) Patent No.: US 8,852,250 B2
(45) Date of Patent: Oct. 7, 2014

(54) GRAFT FIXATION IMPLANT

(75) Inventors: Giuseppe Lombardo, New Port Richey, FL (US); Jessica Brown, St. Petersburg, FL (US); P. Ercell Sherman, Bakersfield, CA (US); Andrew Kam, Odessa, FL (US)

(73) Assignee: Linvatec Corporation, Largo, FL (US)

( * ) Notice: Subject to any disclaimer, the term of this patent is extended or adjusted under 35 U.S.C. 154(b) by 1543 days.

(21) Appl. No.: 11/804,195

(22) Filed: May 17, 2007

(65) Prior Publication Data

US 2007/0270857 A1 Nov. 22, 2007

Related U.S. Application Data (60) Provisional application No. 60/801,314, filed on May 18, 2006, provisional application No. 60/855,853, filed on Nov. 1, 2006.

(51) Int. Cl.
*A61B 5/00* (2006.01)
*A61B 17/04* (2006.01)

(52) U.S. Cl.
CPC ..... *A61B 17/0401* (2013.01); *A61B 2017/0414* (2013.01); *A61B 2017/0409* (2013.01); *A61B 2017/0417* (2013.01)
USPC ...................................................... 606/300

(58) Field of Classification Search
USPC ............... 606/139, 232, 74, 80, 148, 300; 623/13.11
See application file for complete search history.

(56) References Cited

U.S. PATENT DOCUMENTS

| | | | | | |
|---|---|---|---|---|---|
| 444,317 | A | * | 1/1891 | Potter | 174/166 R |
| 551,032 | A | * | 12/1895 | Hemphill | 248/68.1 |
| 3,409,014 | A | * | 11/1968 | Shannon | 606/148 |
| 4,583,541 | A | * | 4/1986 | Barry | 606/286 |
| 4,896,668 | A | * | 1/1990 | Popoff et al. | 606/74 |
| 5,087,260 | A | * | 2/1992 | Fixel | 606/65 |
| 5,203,787 | A | | 4/1993 | Noblitt et al. | |
| 5,269,809 | A | | 12/1993 | Hayhurst et al. | |
| 5,306,301 | A | | 4/1994 | Graf et al. | |
| 5,356,413 | A | * | 10/1994 | Martins et al. | 606/75 |
| 5,505,735 | A | * | 4/1996 | Li | 623/13.14 |
| 5,519,921 | A | * | 5/1996 | Templer, Jr. | 24/130 |
| 5,607,424 | A | * | 3/1997 | Tropiano | 623/17.16 |
| 5,645,588 | A | | 7/1997 | Graf et al. | |
| 5,665,088 | A | * | 9/1997 | Gil et al. | 606/74 |
| 5,665,089 | A | * | 9/1997 | Dall et al. | 606/71 |
| 5,693,060 | A | * | 12/1997 | Martin | 606/148 |
| 5,769,894 | A | | 6/1998 | Ferragamo | |
| 5,941,881 | A | * | 8/1999 | Barnes | 606/71 |
| 5,964,764 | A | * | 10/1999 | West | 606/232 |
| 6,066,141 | A | * | 5/2000 | Dall et al. | 606/74 |
| 6,086,591 | A | * | 7/2000 | Bojarski | 606/64 |

(Continued)

*Primary Examiner* — Christian Sevilla (57) ABSTRACT

The subject invention is a fixation device or anchor intended to secure a graft ligament or other soft tissue repair. The device is designed to be attached to a graft ligament and to secure the graft within a bone tunnel by extending transversely across the opening of the tunnel. In certain procedures the device is intended to pass through a bone tunnel in an orientation generally aligned with the tunnel and then turn transversely. The device has an inherent tendency to rotate upon exiting the tunnel to thereby become automatically transversely aligned with the tunnel and the graft ligament. The rotation is due to a moment automatically created as a resultant of forces applied to the anchor by a pulling-suture via a laterally offset aperture joining the pulling-suture to the anchor.

11 Claims, 11 Drawing Sheets

(56) References Cited

U.S. PATENT DOCUMENTS

| | | | |
|---|---|---|---|
| 6,099,568 A * | 8/2000 | Simonian et al. | 623/13.11 |
| 6,110,207 A | 8/2000 | Eichhorn et al. | |
| 6,193,754 B1 | 2/2001 | Seedhom | |
| 6,440,134 B1 | 8/2002 | Zaccherotti et al. | |
| 6,473,654 B1 * | 10/2002 | Chinn | 607/126 |
| 6,517,578 B2 | 2/2003 | Hein | |
| 6,533,802 B2 | 3/2003 | Bojarski et al. | |
| 6,833,005 B1 | 12/2004 | Mantas et al. | |
| 7,097,654 B1 | 8/2006 | Freedland | |
| 2004/0153153 A1 | 8/2004 | Elson et al. | |
| 2004/0254593 A1 * | 12/2004 | Fallin et al. | 606/148 |
| 2005/0277961 A1 | 12/2005 | Stone et al. | |
| 2006/0058795 A1 * | 3/2006 | Boyd | 606/69 |
| 2006/0241613 A1 * | 10/2006 | Bruneau et al. | 606/69 |

* cited by examiner

FREE BODY DIAGRAM

DURING PASSAGE
AXIAL FORCES
ARE PRESENT AND
OVERCOME MOMENT

AFTER PASSAGE
GUIDE SUTURE IS
RELEASED

ND FIXATION IMPLANT

The present application is related to and claims the benefit under 35 USC 119(e) of U.S. Provisional Applications Ser. No. 60/801,314 filed May 18, 2006 and Ser. No. 60/855,853 filed Nov. 1, 2006.

FIELD OF THE INVENTION

The invention relates generally to devices and procedures for securing artificial graft ligaments within bone tunnels. More particularly, the invention relates to devices and procedures for securing graft ligaments in the repair of the anterior cruciate ligaments and posterior cruciate ligaments of the knee.

BACKGROUND OF THE INVENTION

Due to the frequency of injury to various ligaments such as the anterior cruciate ligament (ACL), especially in sports, and similar injury to other ligaments and related structures, there is a great deal of prior art dealing with a replacement of these structures with ligament grafts. Much of this prior art is concerned with ensuring proper placement of bone tunnels drilled in the bones intended to receive the opposed ends of the graft ligament, such as the tibia and femur, with proper preparation of the surgical site, i.e., by removing sufficient bone to allow the graft to function properly, and with preparation of suitable graft ligaments, commonly by harvesting donor soft tissue or bone/tendon/bone structures from the patient. See generally, "The Paramax ACL Guide System Surgical Technique", a brochure published by Linvatec Corporation of Largo, Fla. in 1992, and incorporated by reference herein, which provides useful background on one type of overall ACL replacement procedure. Other sources of replacement ligaments, including allograft and autograft ligament substitutes, are within the skill of the art and are intended to be included within the term "graft ligament" as used herein.

The present invention does not address these aspects of ACL reconstruction, but instead addresses the problem of securely anchoring the graft ligament in the bone tunnels. More specifically, the present invention relates to improvements in devices to be disposed at the outer ends of bone tunnels to provide a fixing point for securing an end of a graft ligament in place.

The prior art shows anchors for ligaments wherein the ligament is sutured to an anchor configured to abut the outer opening of the bone tunnel, and remain outside the bone tunnel. See for example Graf et al. U.S. Pat. No. 5,306,301 disclosing various elongated bodies intended to be passed through the bone tunnels and rotated after exiting the tunnels, so as to be retained against the outer surface of the bone. See also U.S. Pat. No. 5,139,520 to Rosenberg. This category of devices includes generally elongated relatively thin plates designed to be aligned with a bone tunnel while passing through the bone tunnel and then designed to be manipulated into a transverse position across the bone tunnel to prevent a graft attached to the device from being detached from the bone tunnel. These devices include a plurality of apertures designed to receive graft retaining sutures as well as manipulating sutures intended to manipulate the device into a transverse orientation. The manipulation of such devices is sometimes challenging and there exists a need in the art for improvements in graft fixation devices and procedures. Furthermore, such devices are not easily repositioned or removed once set in place. Accordingly, there exists a need for devices which can be easily repositioned.

It is an object of this invention to provide a graft ligament anchor capable of minimizing the degree of manipulation required to set the anchor transversely to the bone tunnel. It is also an object of this invention to provide a graft ligament anchor capable of being easily repositioned or removed.

SUMMARY OF THE INVENTION

These and other objects are achieved by a preferred embodiment disclosed herein which is a graft fixation implant comprising an elongated body having a proximal end, a distal end, a central portion interposed between the proximal and distal ends, a longitudinal axis extending through the proximal and distal ends and a transverse axis extending through the central portion. The body has an axially aligned proximal aperture in the proximal end and an axially aligned distal aperture in the distal end. Both apertures extend through the body and are within a common plane which includes the longitudinal axis. A pulling-suture receiving aperture extends through the central portion and is aligned parallel to the common plane and spaced laterally from the longitudinal axis. A pulling-suture threaded through the pulling-suture receiving aperture and pulled distally will create a turning moment in the implant.

BRIEF DESCRIPTION OF THE DRAWINGS

Various examples of the present invention will be discussed with reference to the appended drawings. These drawings depict only illustrative examples of the invention and are not to be considered limiting of its scope.

DESCRIPTION OF THE PREFERRED EMBODIMENT

Figure 1:
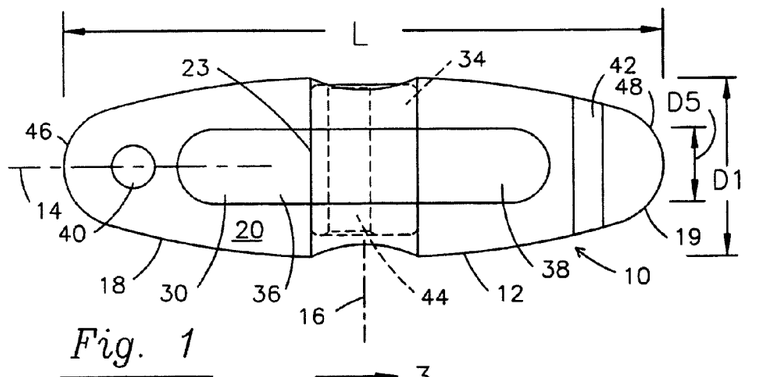
FIG. 1 is a top plan view of graft fixation anchor constructed in accordance with the principles of this invention.

FIG. 1 is a top plan view of a preferred embodiment of a graft fixation implant 10 constructed in accordance with the principles of this invention. The terms "graft fixation implant" and "ligament anchor" and "anchor" may be used interchangeably herein. Ligament anchor 10 comprises a generally elliptical body 12 (when viewed in a top plan view), formed from biocompatible, absorbable or non-absorbable materials having a longitudinal axis 14, a transverse axis 16 and proximal and distal ends 18 and 19. Body 12 lies generally in the plane of the paper showing FIG. 1. The proximal end 18 is that portion of body 12 from axis 16 to the left in FIG. 1. Similarly, the portion to the right is distal end 19. The profile in this top plan view may be rectilinear or more rectilinear and less elliptical for certain applications.

Figure 2:
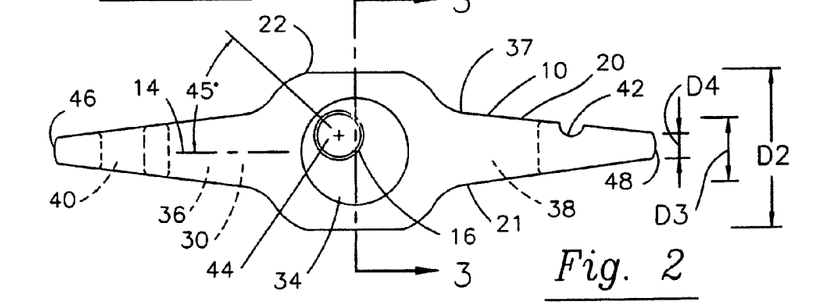
FIG. 2 is a front elevation view of FIG. 1.

As best seen in FIGS. 1 and 2, anchor 10 also has top and bottom surfaces 20 and 21, respectively, and a central body portion 22 interposed between ends 18 and 19. Central body portion 22 is partially hemispherical in this view and, therefore, has a generally truncated circular profile when viewed from the side as shown in FIG. 2. Anchor 10 further comprises a slot 30 axially aligned with axis 14 and extending proximally and distally on either side of transverse axis 16. A core 23 extends between opposing sides of the anchor body as shown in FIG. 1 and divides slot 30 into a proximal aperture 36 and a distal aperture 38, both of which are within the common plane of body 12 (i.e. in the plane of the paper showing FIG. 1). The term "within" a plane as used herein means that the aperture is a two-dimensional opening lying in a plane such that an object inserted through the aperture will be oriented other than parallel to the plane. Proximal end 18 is further provided with a transverse guiding-suture receiving aperture 40 extending between top surface 20 and bottom surface 21. Distal end 19 is provided with a transverse identifying mark in the form of a groove, notch or other indicia 42.

Figure 3:
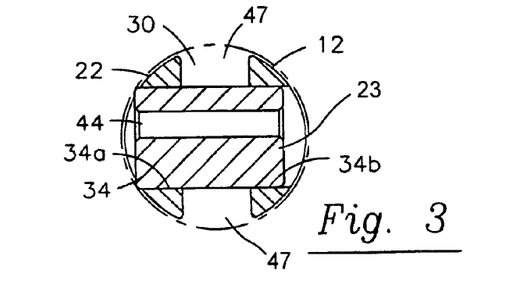
FIG. 3 is a cross-sectional view of FIG. 2 taken along the lines 3-3.

Central portion 22 is provided with a pulling-suture receiving aperture 44 situated parallel to transverse axis 16 and perpendicular to axis 14. In a preferred embodiment central portion 22 is formed in part by a central core 23 which is in the form of a transverse, cylindrical pin 34 (which may be formed of the same material as the body of anchor 10) press fit into apertures 34a and 34b formed into the sides of body 12 on either side of slot 30. As will be understood below, pin 34 is assembled with body 12 in such a way as to cause aperture 44 to be aligned at a 45° angle relative to the axis 14. While in the preferred embodiment a single aperture 44 is utilized, as will be understood below that another aperture (best seen in FIG. 19) could be situated diametrically opposite in the lower right quadrant of pin 34. Pin 34 may be laterally, asymmetrically received in apertures 34a and b, as shown in FIGS. 1 and 3, or may be symmetrically situated (not shown). Core 23 defines a channel 47 above and below pin 34, as seen in FIG. 3, intended to receive a graft or graft retaining member.

Figures 4, 5:
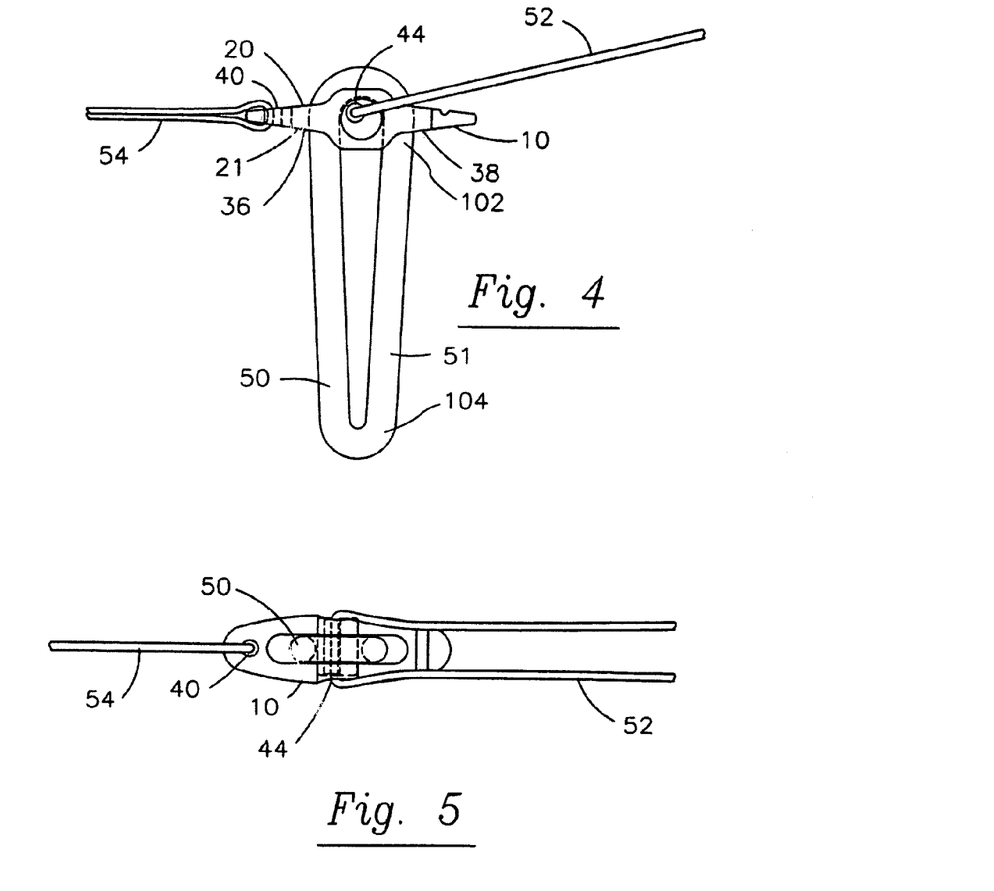
FIG. 4 is a front elevation view of the anchor embodiment of FIG. 2 showing it assembled with other elements.
FIG. 5 is a top plan view of FIG. 4.

As best seen in FIGS. 4 and 5, anchor 10 is designed for certain surgical procedures to operate with a graft retaining member 50, a distally extending pulling-suture 52 received in aperture 44 and a proximally extending guiding-suture 54 received in aperture 40. Graft retaining member 50 is, in a preferred embodiment, slidable in slot 30 and around core 23 within apertures 36 and 38, and is in the form of an endless loop 51 formed of flexible suture or tape, woven material and the like. To facilitate assembly of graft retaining loop 51 with anchor 10, pin 34 is assembled with body 12 and inserted through the graft retaining loop 51 after the loop is inserted into slot 30. Alternatively, as explained below, body 12 could be formed in one piece with proximal and distal apertures 36, 38 and retaining loop 51 could then be attached. In this case aperture 44 would still be aligned preferably at a 45° angle relative to the axis 14. As will be understood below, in another alternate embodiment the graft retaining member could be the graft itself or a suture tying the graft and core 23 together.

Loop 51 may be formed in a variety of ways and from a variety of biocompatible, absorbable or non-absorbable materials. In the preferred embodiment, loop 51 is an endless loop woven from any biocompatible suture material including, but not limited to fibers of polyester, polyethylene or ultra high molecular weight polyethylene material. Loop 51 could be formed of one or more strands of suture simply knotted together if desired. Alternatively, one continuous piece of monofilament or braided suture could be looped several times around core 23 with the ends simply tied together or otherwise joined to form an endless loop. Loop 51 could be an endless loop of flexible tape or tubing. Loop 51 is intended to fit within apertures 36 and 38 (and channel 47) thereby causing it to engage core 23 and extend away from anchor 10 as schematically shown in FIG. 4. To facilitate an explanation of the operation of anchor 10 the portion of loop 51 in contact with anchor 10 will be referred to as distal loop end 102 and a portion of loop 100 farthest away from anchor 10 will be referred to as proximal loop end 104. Distal loop end 102 may extend above the body of anchor 10 when it is properly seated in channel 47.

Anchor 10 has a maximum width D1 and D2 equal to the size of central portion 22 as will be understood below and by reference to FIGS. 1 and 2. Diameters D1 and D2 must be equal to or less than the diameter of the bone tunnels through which anchor 10 must pass. Anchor 10 has a length L which is greater than the diameter of the tunnel. In the preferred embodiment shown in FIGS. 1 and 2 the ends 18 and 19 have a width D3 in the side elevation view at the point 37 where the ends meet central portion 22. The width of ends 18 and 20 taper down between point 37 and rounded tips 46 and 48, respectively, to a width D4. In the preferred embodiment length L is 0.54 inches (13.71 mm), width D1 is 0.173 inches (4.39 mm), thickness D2 is 0.155 inches (3.93 mm). The diameter of cylindrical pin 34 is 0.0984 inches (2.49 mm).

The width D5 of slot 30 is 0.070 inches (1.77 mm). The thickness D3 of proximal and distal ends at the point 37 where they meet central portion 22 are 0.069 inches (1.75 mm) and D4 is 0.025 inches (0.635 mm). It will be understood that the tip ends 46 and 48 are preferably rounded to conform to the cylindrical shape of the bone tunnels.

Figure 6:
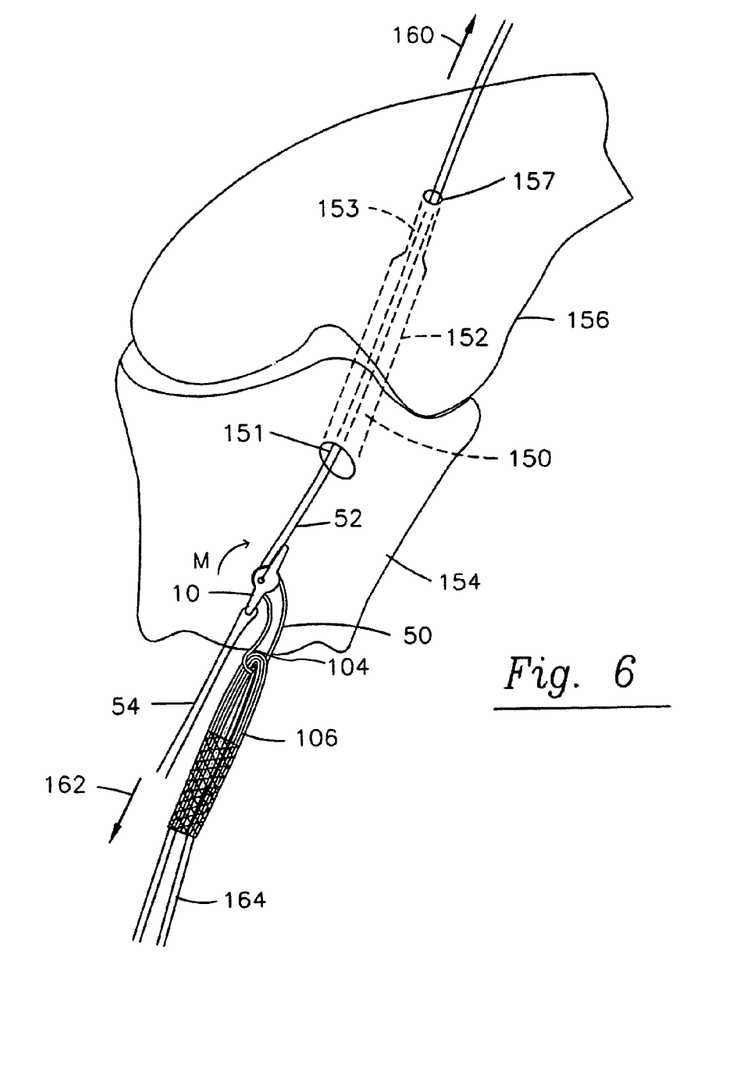
FIG. 6 is a schematic view of the anchor of FIG. 5 being used in a surgical procedure.

The operation of anchor 10 will be explained by reference to FIGS. 6 through 11 in terms of using anchor 10 to attach a graft ligament to repair an anterior cruciate ligament although it will be understood that anchor 10 may also be used for other graft attachments. The procedure begins with the conventional creation of bone tunnels 150 and 152 in tibia 154 and femur 156, respectively. The proximal, entrance end of the tibial tunnel is at 151. Femoral tunnel 152 has a smaller diameter bore 153 formed between the distal end of tunnel 152 and the lateral surface of the femur, and the bore 153 has a distal, exit opening 157 on the lateral femoral surface. The formation of these tunnels is well known to those skilled in the art. The diameter of the tibial and femoral tunnels 150 and 152 may be on the order of seven to twelve millimeters while the diameter of bore 153 may be on the order of 5 mm. After preparation of the graft ligament construct 106, also well known to those skilled in the art, it is attached to proximal loop end 104. In the case of a soft tissue graft (as shown in FIG. 6), such attachment may simply be accomplished by folding the soft tissue graft through proximal loop end 104. Alternatively, the graft ligament could be sutured to proximal loop end 104. (In the case of a bone-tendon-bone graft, the graft could be sutured to the loop.) A pulling-suture 52 is passed through transverse aperture 44 and a guiding-suture 54 is passed through aperture 40. While aperture 40 is shown to extend perpendicularly to the plane of anchor 10 it could extend in any other orientation. The pulling-suture will be used to pull anchor 10, loop 51 and graft construct 106 into femoral tunnel 152 while the guiding suture will be used to maintain alignment of anchor 10 during its passage through the tunnels. Because the length L of anchor 10 is greater than the diameter of tunnels 150, 152 and 153, anchor 10 must be generally aligned with the tunnels in order to pass through from the tunnel entrance to the tunnel exit. The insertion of anchor 10 and graft construct 106 in the tunnels is accomplished by first passing the pulling-suture 52 through bone tunnels 150, 152 and 153 in a conventional manner and then pulling the suture 52 in a distal direction 160 while slightly pulling guiding-suture 54 in a proximal direction 162.

Figure 7:
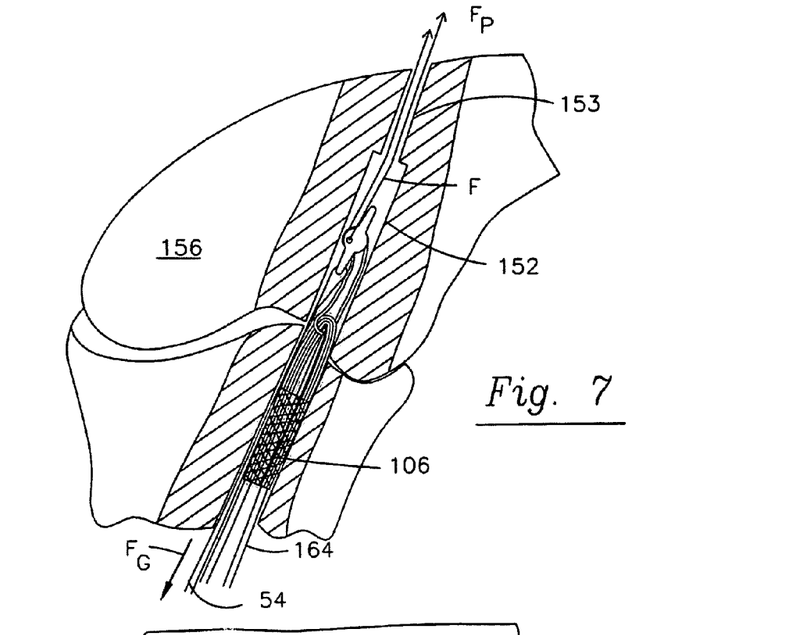
FIG. 7 is a schematic view showing another step in the method of using the invention to attach a graft ligament within a bone tunnel.
Figure 8:
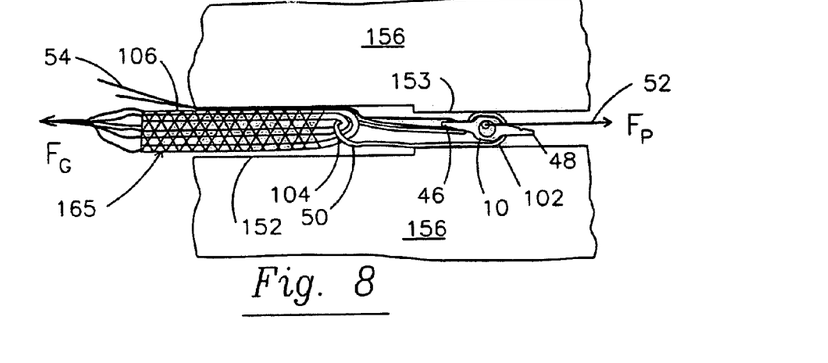
FIG. 8 is another step in the method of using the invention to attach a graft ligament within a bone tunnel.
Figure 9:
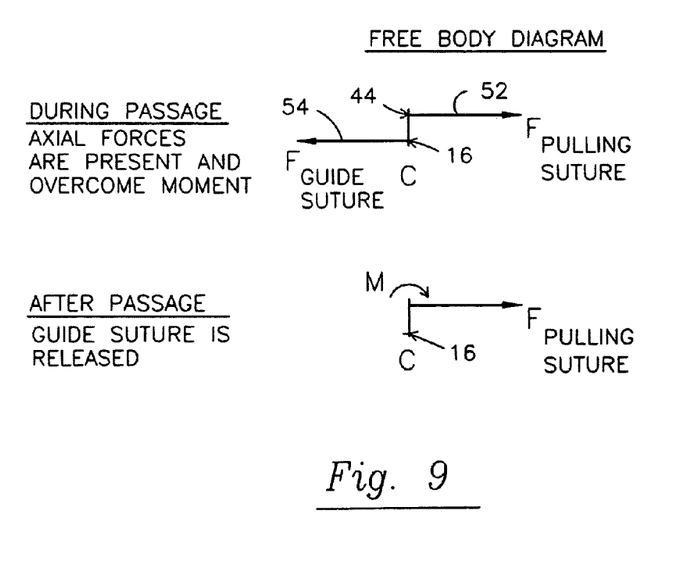
FIG. 9 is a pair of force diagrams illustrating the forces acting on the implant shown in FIG. 7 during implantation.
Figure 10:
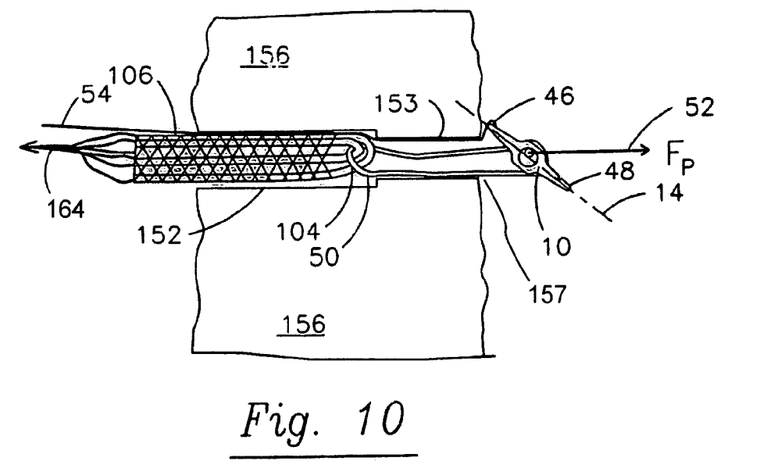
FIG. 10 is another step in the method of using the invention to attach a graft ligament within a bone tunnel.

As shown in FIGS. 7, 8 and 9, during passage of the anchor 10, loop 51 and graft construct 106 pass through tunnels 150 and 152, the manner in which loop 51 is attached to and interacts with anchor 10 creates moment M, best seen in FIG. 6, which tends to rotate anchor 10 about its transverse axis 16. During passage through the tunnels the graft retaining loop 51 generally conforms to the shape shown in FIGS. 7 and 8. That is, the loop curves around core 23 adjacent the distal loop end 102, extends through proximal and distal apertures 36 and 38 and extends proximally toward graft 106. As shown in FIG. 9, during passage, while the anchor is being pulled through the tunnels the force $F_P$ of the pulling-suture 52 is slightly greater than the force $F_G$ of the guiding-suture 54 and their relative magnitudes are sufficient to keep the rotational forces in equilibrium so that the anchor is prevented from significantly rotating about its axis 16 during passage through the tunnel. During passage of the graft construct through the tunnels 150 and 152, the forces are in rotational equilibrium and the graft construct 106 is simply pulled along with the anchor 10.

Figure 11:
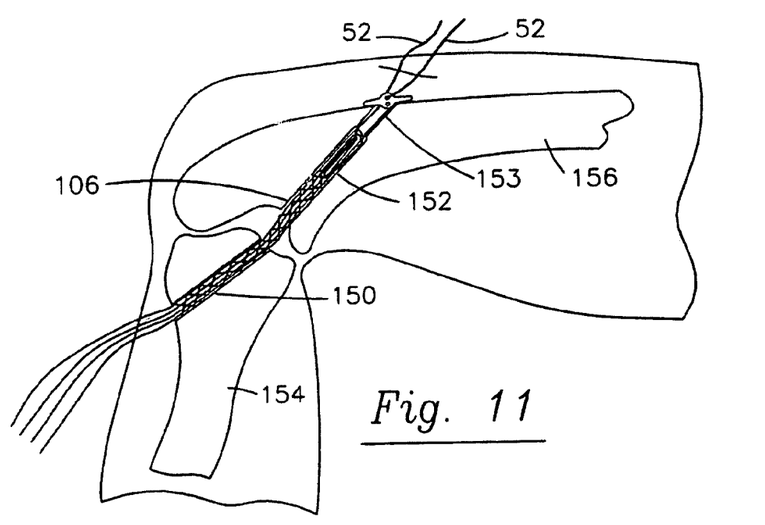
FIG. 11 is another step in the method of using the invention to attach a graft ligament within a bone tunnel.

The laterally offset position of the pulling-suture receiving aperture 44 also creates a clockwise moment about axis 16. In the preferred embodiment the pulling-suture receiving aperture 44 is situated in the upper left quadrant of pin 34 as shown in FIG. 2. The location of indicia 42 provides a visual indication to the user: if anchor 10 is pulled through the bone tunnel with indicia 42 on the leading or distal end of the anchor when the loop 51 extends from the bottom of the anchor (FIG. 4), the aperture 44 will be positioned properly to create the desired moments. The contact between the loop and the tunnel wall or between the graft and the tunnel wall will create additional clockwise moments about axis 16 as the anchor is pulled through the tunnel. Because of the relatively smaller diameter of the tunnel 153, frictional contact may cause this moment to be increased as the loop contacts the tunnel wall. This may cause ends 46 and 48 to slide along or dig into the tunnel wall. Guiding-suture 54 can be pulled proximally to overcome any excessive rotation of anchor 10 which might cause distal end 48 to dig into the tunnel wall. As shown in FIG. 7 when anchor 10 is in femoral tunnel 152 it is generally aligned with the tunnel axis by virtue of opposing tension between pulling-suture 52 and guiding-suture 54. The graft construct is indirectly pulled along distally with the anchor. At the transition between tunnels 152 and 153, by virtue of the relative tunnel diameters, the aligned anchor is able to enter tunnel 153 as shown in FIG. 8 while the graft construct cannot. The distance between the proximal entrance 151 of the tibial tunnel and the distal exit 157 of the femoral tunnel can be determined by conventional means so that assembly of the graft construct and loop 51 can be made long enough so that anchor 10 can exit distal end 157 of the femoral tunnel and be properly seated at the tunnel opening as shown in FIG. 11.

When the distal end of the graft construct bottoms out at the end of femoral tunnel 152 the guiding-suture 54 is released. Moment M created by pulling-suture 52 then begins to automatically rotate anchor 10 about axis 16. As schematically shown in FIG. 9, after passage, as anchor 10 continues to exit tunnel 153 the moment M created by the pulling-suture 52 will cause further rotation of anchor 10 about its axis 16. When suture 52 is pulled sufficiently to cause the proximal end 18 of anchor 10 to clear the tunnel, anchor 10 will, by virtue of moment M, automatically flip to a position where its major axis 14 is substantially transverse to the tunnel as shown approximately in FIG. 10. No manipulation of pulling-suture 52 is necessary to accomplish this change in orientation. The substantially transverse orientation of anchor 10 at this point prevents the anchor from passing back into the tunnel. A proximally directed pull on trailing suture(s) 164 attached to the proximal end of the graft construct 106 will complete any necessary rotation of anchor 10 into a transverse position and seat the anchor at the distal opening 157 of the tunnel as best seen in FIG. 11. In this position the outer partially hemispherical surfaces of central portion 22 will seat in the tunnel opening 157 to prevent excessive lateral movement of the anchor relative to the tunnel. Anchor 10 can be produced with a variety of loop lengths defined as the distance between the loop ends 102 and 104 as measured on the inside surface of the loop. This will accommodate various graft and tunnel lengths that may be encountered during a surgical procedure.

In the preferred embodiment central portion 22 is enlarged in the lateral direction relative to proximal and distal ends 18 and 19 as best seen in FIG. 2. This facilitates the laterally offset placement of aperture 44 relative to axis 14 which enhances the moment that can be produced by the pulling-suture. It will be apparent that certain designs of anchor 10 could include an offset aperture 44 without enlarging the central portion relative to the proximal and distal ends of the anchor.

Because anchor 10 is an elongated, generally planar device it is preferably aligned on the lateral femoral surface with the axis of the femur. Anchor 10 could be made with a predetermined transverse radius of curvature to conform to the transverse arcuate nature of the surface of the femur at the point where the femoral tunnel intersects the lateral surface.

Figure 12:
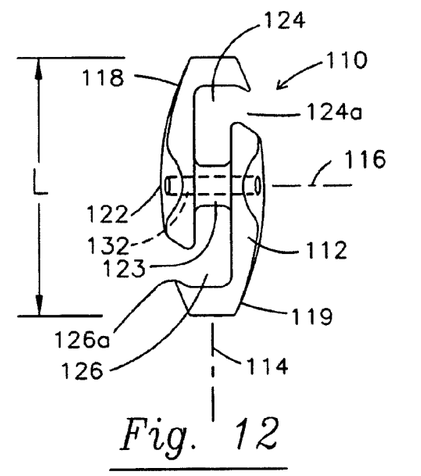
FIG. 12 is a front elevational view of another alternate embodiment of the anchor shown in FIG. 1.
Figure 13:
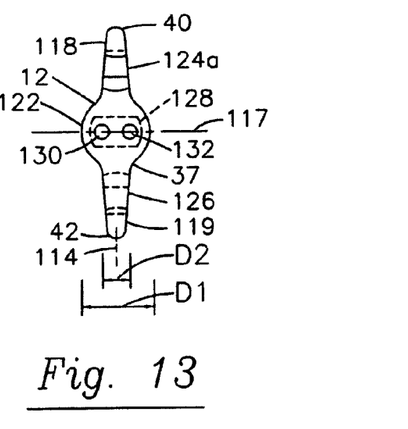
FIG. 13 is a side view of FIG. 12.

In an alternate embodiment the ligament anchor is embodied as anchor 110 shown in FIGS. 12 and 13. Anchor 110 is a one-piece, generally elliptical body 112 having a longitudinal axis 114, a transverse axis 116 and proximal and distal ends 118 and 119, respectively. A generally circularly profiled central portion 122 is provided between ends 118 and 119. Symmetrical loop-receiving apertures 124 and 126 are provided with access slots or openings 124a and 126a, respectively, for easy access to enable loading a graft retaining member (similar to member 50 shown in FIG. 4) into apertures 124 and 126. Central portion 122 has a core 123 connecting opposing sides of the central portion 122. Core 123 may have a generally rectangular profile as best seen in FIG. 13. Core 123 and central portion 122 are provided with a pair of transverse pulling-suture apertures 130 and 132, each laterally spaced from axis 114. In this embodiment both pulling-suture receiving apertures 130 and 132 are aligned on transverse axis 117. It will be understood that an endless rope like loop 51 can be placed in apertures 124 and 126 so it can be supported by central core 123. A guiding-suture (not shown) may be received in whichever aperture 124 or 126 is on the proximal end of the anchor during insertion.

Figure 14:
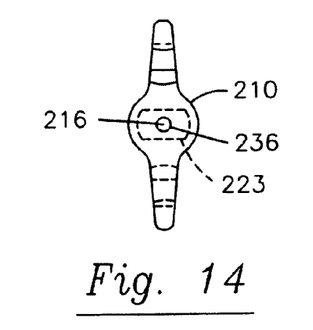
FIG. 14 is a side view of an alternate embodiment of the anchor shown in FIG. 12.

As shown in FIG. 14, an alternate embodiment of the invention comprises anchor 210 which is identical to anchor 110 except that core 223 is provided with a single pulling-suture aperture 236 which can be aligned with axis 216.

Figure 15:
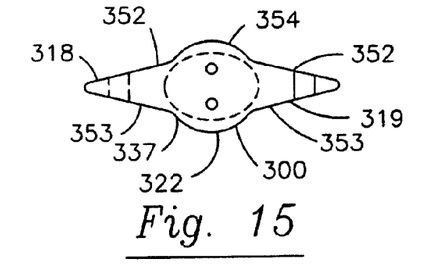
FIG. 15 is a front elevational view of another alternate embodiment of the anchor.

In another alternate embodiment shown in FIG. 15, anchor 300 is formed such that the width of ends 318 and 319 at point 337 approaches the point where the top and bottom surfaces 352 and 353, respectively, of ends 18 and 19 are almost tangent to the surface 354 of central portion 22. It will be understood below that it is preferable if surfaces 352, 353 do not extend outwardly beyond surface 354 so that the curved surface of central portion 322 can partially be seated in the tunnel opening 157. The pulling-suture receiving apertures are situated as in FIG. 13 and the remaining elements are comparable to those shown in FIG. 12.

Figure 16:
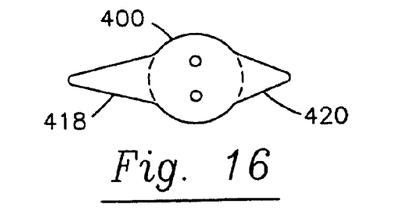
FIG. 16 is a front elevational view of another alternate embodiment of the anchor.

In another alternate embodiment shown in FIG. 16 anchor 600 has non-symmetrical ends 618 and 620. The remaining elements are comparable to those shown in FIG. 12.

Figure 17:
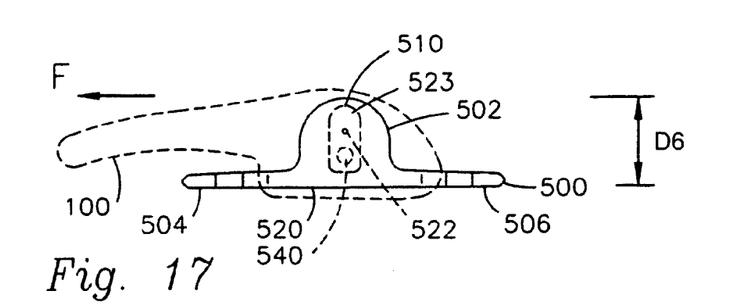
FIG. 17 is a top plan view of an alternate embodiment of the anchor shown in FIG. 1.

As shown in FIG. 17 another embodiment of the invention is anchor 500 comprising a longitudinally symmetrical but transversely asymmetrical body 502 having proximal and distal ends 504 and 506 with apertures as noted above in anchor 110. Loop 100 is schematically shown threaded along the path it would generally follow during the action of pulling anchor 500 through a tunnel. The diameter D6 and the distance of outer end 510 of core 523 from the base surface 520 cooperate to produce a significant moment about transverse axis 522 when a force F is applied to loop 100. As with all anchor embodiments, the anchor dimensions, including its length and diameter D6 may be changed to vary the moments created for various applications. In all embodiments this moment is due to the interaction of the tunnel, the loop at point 510 (or its equivalent) of core 523 and a pulling-suture passed through pulling-suture receiving aperture 540.

Figures 18, 19, 20:
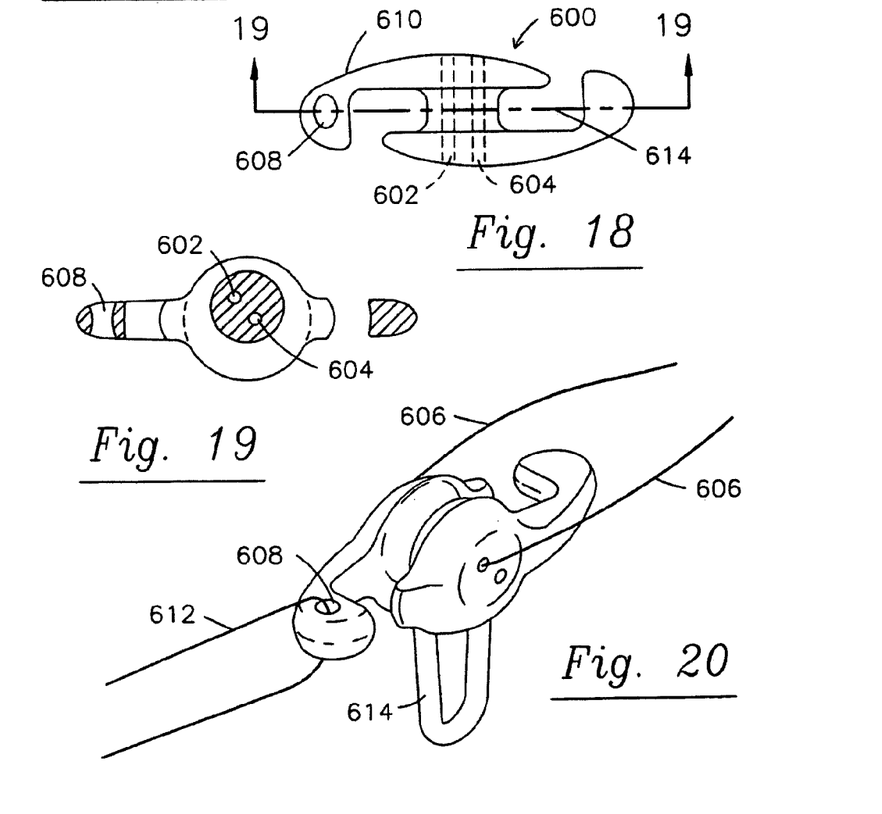
FIG. 18 is a top plan view of an alternate embodiment of the anchor shown in FIG. 1.
FIG. 19 is a cross-sectional view of FIG. 18 taken along the line 19-19.
FIG. 20 is a perspective view of the anchor of FIG. 18 assembled with other components.

FIGS. 18-20 illustrate an implant 600 which is an alternative embodiment of the implant 10 of FIG. 1. Implant 600 includes one or more pulling-suture receiving apertures 602 and 604, through a central portion transverse to the major axis 614 of the device for receiving one or more pulling-sutures 606 to pull the implant 600 through the bone tunnel. The implant 600 further includes a guiding-suture receiving aperture 608 through proximal end 610 for receiving a guiding-suture 612. The implant 600 receives a graft loop 614.

Figure 21:
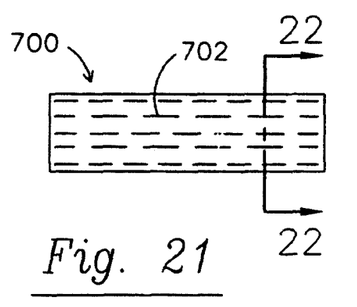
FIG. 21 is a side elevation view of a billet of material from which the anchor embodiments of the invention may be made.
Figure 22:
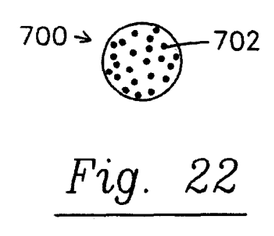
FIG. 22 is a cross-sectional view of the billet of FIG. 21 taken along line 22-22.

The implant of the present invention can be made of one or more pieces and from a variety of materials. Some materials have a strength orientation due to processing of the material (e.g. drawing of the material) and/or due to structural elements in the material (e.g. reinforced materials). For example, reinforced polymers are known in which fiber or other reinforcing elements extend unidirectionally through the polymer matrix. The reinforcing elements are herein referred to as fibers, but may be other structures. Some extruded or drawn polymers are self-reinforced by embedding fibers of the material within a matrix of the same material. Reinforcement is also possible through orientation of the polymer structures themselves as shown, for example, by U.S. Pat. No. 4,968,317 (Tormala et al.), assigned to the assignee hereof and incorporated by reference herein. FIG. 21 illustrates a billet 700 of self-reinforced polymer showing schematically the longitudinal orientation of the reinforcing polymers or fibers 702 resulting in a longitudinal strength orientation. FIG. 22 illustrates a cross section of the billet 700 showing the longitudinal polymers or fibers 702 in an end-wise cross-sectional view.

Figure 23:
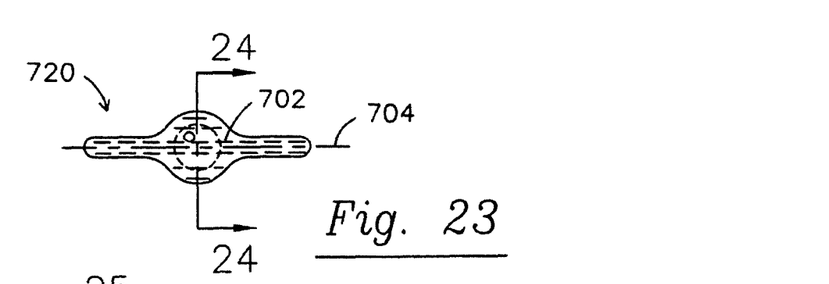
FIG. 23 is a side elevation view of an implant according to the present invention made in one piece of self-reinforced polymeric material.
Figure 24:
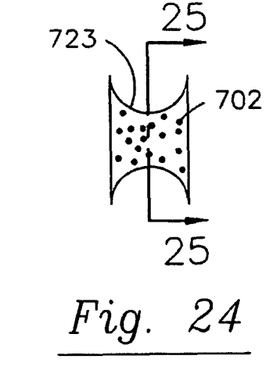
FIG. 24 is a cross-sectional view of the implant of FIG. 23 taken along line 24-24.
Figure 25:
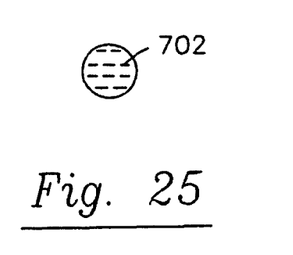
FIG. 25 is a cross-sectional view of the implant of FIG. 23 taken along line 25-25 of FIG. 27.

FIGS. 23-25 illustrate an anchor 720 according to the present invention made as a single piece from the billet of FIG. 21. Anchor 720 may be machined from the billet or molded so as to keep the reinforcing polymers or fibers 702 generally parallel to axis 704. It will be understood that the various apertures and other structures shown in FIGS. 1 and 2 or other embodiments could be formed into anchor 720 although they are omitted in FIG. 23. The cross-sectional views of FIGS. 24 and 25 further illustrate how the orientation of the material is uniform throughout the implant. Since anchor 720 is formed on one piece, its core section 723 has longitudinally extending polymers or fibers 702. The direction of orientation of these structures may be varied.

Figures 26, 27, 28, 29:
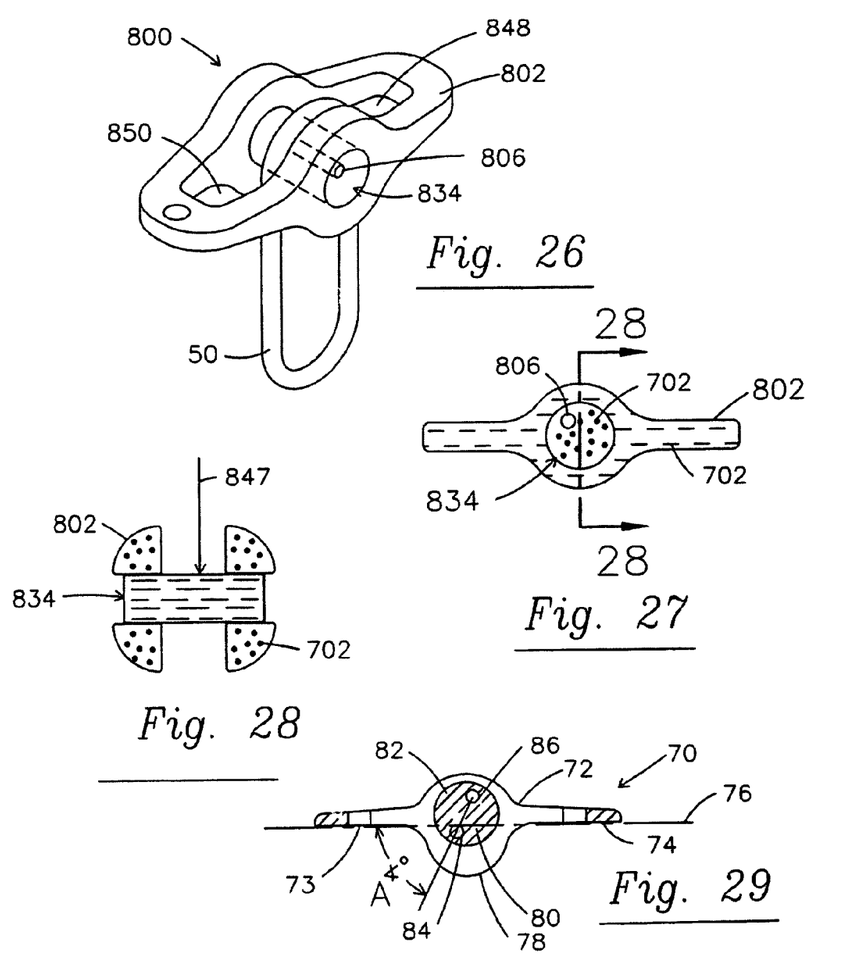
FIG. 26 is a perspective view of an alternative embodiment of the graft fixation implant of FIG. 1.
FIG. 27 is a side elevation view of the implant of FIG. 26.
FIG. 28 is a cross-sectional view of the implant of FIG. 27 taken along line 28-28.
FIG. 29 is a cross-sectional schematic view of an alternate embodiment of FIG. 2.

FIGS. 26-28 illustrate an implant 800 according to the present invention made as a two-piece assembly from the billet 700 of FIG. 21. The implant 800 comprises a body 802 and a cross pin 834 joined to the body such as by an interference fit, solvent bonding, ultrasonic welding, and/or other joining methods. The body 802 is formed (machined, molded, etc.) from the billet 700 with a longitudinal strength orientation (best seen schematically in FIG. 27) relative to the body 242. The pin 834 is likewise formed from the billet 700 with a longitudinal strength orientation relative to the pin 834 and with a pulling-suture receiving aperture 806. Upon assembly of the body 802 and pin 834, the body and pin strength orientations are transverse to one another as best seen in FIGS. 27 and 28. Thus, the two-piece assembly permits the best use of the oriented material by orienting the axis of greatest strength for each part in the most advantageous direction. As shown in FIG. 29, the load 847 placed on the pin 834 by the graft loop 50 tends to bend the pin 834 placing the top of the pin in longitudinal compression and the bottom of the pin in longitudinal tension. The longitudinal strength orientation of the pin is the strongest orientation under these load conditions. The implant 800 further is formed with closed apertures 848 and 850 such that the graft loop 50 is captive on the implant 800. The two piece assembly permits capturing a pre-formed loop 50 within the apertures 848 and 850 by first inserting the loop 50 and then inserting the pin 834 to secure the loop to the body 802.

In another alternate embodiment shown in FIG. 29 anchor 70 comprises a body 72 having an elliptical profile in plan view (not shown, but like FIG. 1). However, when viewed from the side as in FIG. 29, anchor 70 comprises ends 73 and 74 which have their bottom sides aligned along axis 76. Core 82 has a circular cross-section in side view and has spaced pulling-suture receiving apertures 84 and 86 aligned on opposite sides of core axis 80 at an angle A relative to axis 76. The remaining portions of anchor 70 are similar to anchor 110.

Figure 30:
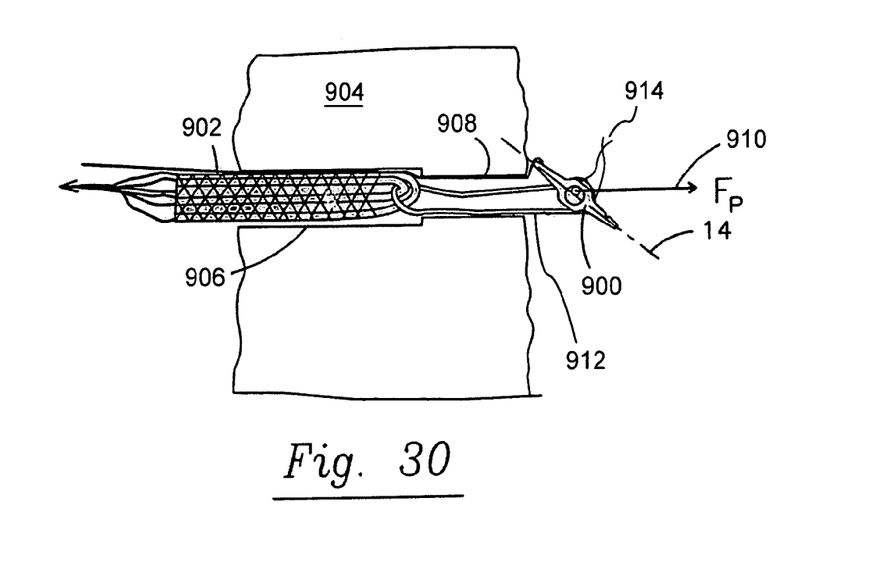
FIG. 30 is a schematic view of a method of using the anchor of FIG. 1 by attaching it to a graft by means of a knotted suture.

It will be understood that anchor 10 and its alternate embodiments may be used in a variety of surgical procedures for the attachment of soft tissue to bone or for attachment of any tissue to a location firm enough to support a transversely oriented anchor. This attachment may even be accomplished without a loop. That is, as shown in FIG. 30, anchor 900, comparable to anchor 10 or any of the other anchor embodiments, may be used without a loop to attach a ligament graft or other soft tissue 902 to a support structure 904 through which a tunnel 906 has been formed. A smaller tunnel 908 could be formed, comparable to tunnel 153 of previous embodiments. Once the graft has been pulled into place by pulling-suture 910 the graft may be attached to anchor 900 by suture 912 knotted at 914. It will be understood that the suture strands pass through the proximal and distal apertures of anchor 900 and are tied around the anchor's core It will be understood by those skilled in the art that numerous improvements and modifications may be made to the preferred embodiment of the invention disclosed herein without departing from the spirit and scope thereof.

The invention claimed is:

1. A graft fixation implant comprising:
   an elongated body having a length parallel to a longitudinal axis and a width parallel to a transverse axis when viewed in a top plan view, a common plane of said elongated body being defined by said longitudinal axis and said transverse axis, and said length being greater than said width, said elongated body comprising:
   three portions positioned along said length, the three portions being a proximal end portion, a distal end portion, and a central portion interposed between said proximal end portion and said distal end portion, the central portion having a width that is enlarged relative to each of said proximal end portion and said distal end portion, each of said proximal end portion and said distal end portion tapering to become relatively narrower while extending from said central portion to a rounded proximal tip and a rounded distal tip, respectively;
   a slot formed through the elongated body, said slot being axially aligned with said longitudinal axis and extending proximally and distally on either side of said transverse axis;
   a generally cylindrical core separating said slot into a proximal aperture and a distal aperture positioned within said proximal end portion and said distal end portion, respectively, said core being aligned with said transverse axis; and
   a pulling-suture receiving aperture extending through said core, a center axis of said pulling-suture receiving aperture being offset from said common plane, being situated parallel to said transverse axis, and being situated perpendicular to said longitudinal axis.

2. A graft fixation implant according to claim 1 further comprising:
   a loop graft retaining member received in said proximal and distal apertures.

3. A graft fixation implant according to claim 1 wherein said transverse axis bisects said central portion when viewed in said top plan view, and wherein said pulling-suture receiving aperture is situated proximally of said transverse axis.

4. A graft fixation implant according to claim 1 further comprising:
   a proximal access opening in said body adjacent said proximal aperture; and
   a distal access opening in said body adjacent said distal aperture.

5. A graft fixation implant according to claim 2 further comprising:
   a longitudinally aligned channel in said central portion, said channel joining said proximal and distal apertures and for receiving a portion of said graft retaining member.

6. A graft fixation implant according to claim 1 further comprising:
   a second pulling-suture receiving aperture extending through said central portion at a location opposite said common plane from said pulling-suture receiving aperture.

7. A graft fixation implant according to claim 1 further comprising an aperture in said proximal end for receiving a guiding-suture which, in use, extends proximally from said proximal end portion.

8. A graft fixation implant according to claim 1 wherein an orienting mark is placed on said body to identify the proper orientation for said body during use.

9. A graft fixation implant according to claim 1 further comprising:
   a pulling-suture received in said pulling-suture receiving aperture.

10. A graft fixation implant according to claim 7 further comprising:
    a guiding suture received in said guiding-suture receiving aperture.

11. A graft fixation implant comprising an elongated body comprising:
    a proximal end portion and a distal end portion being separated from one another by a central portion, each of said proximal end and said distal end having a top surface viewed in a top plan view and a bottom surface viewed in a bottom plan view;
    a width of said central portion being parallel to a transverse axis when viewed in a top plan view;
    a length including said proximal end portion, said central portion and said distal end portion being parallel to a longitudinal axis when viewed in said top plan view, said longitudinal axis bisecting said width, said length being longer than said width, and said longitudinal axis being perpendicular to said transverse axis;
    a thickness of said central portion being perpendicular to said width and said length;
    a common plane being defined by said transverse axis and said longitudinal axis, said common plane bisecting said thickness of said central portion;
    a proximal aperture extending through said top surface and said bottom surface of said proximal end, said proximal aperture being within said common plane;
    a distal aperture extending through said top surface and said bottom surface of said distal end, said proximal aperture being within said common plane;
    a generally cylindrical core positioned in said central portion, said core separating said proximal aperture from said distal aperture, said core being aligned with said transverse axis and
    a pulling-suture receiving aperture being situated in said core and having a center axis spaced laterally from said common plane, wherein said width of said central portion is enlarged relative to each of said proximal end portion and said distal end portion, each of said proximal end portion and said distal end portion tapering to become relatively narrower while extending from said central portion to a rounded proximal tip and a rounded distal tip, respectively.

* * * * *